United States Patent [19]

Commeyras et al.

[11] 4,098,806

[45] Jul. 4, 1978

[54] PROCESS FOR FUNCTIONALIZING PERFLUOROHALOGENOALKANES

[75] Inventors: Auguste Commeyras, Clapiers; Hubert Blancou, Montpellier; Patrice Moreau, Saint Gely du Fesc, all of France

[73] Assignee: Produits Chimiques Ugine Kuhlmann, Paris, France

[21] Appl. No.: 772,107

[22] Filed: Feb. 25, 1977

[30] Foreign Application Priority Data

Mar. 5, 1976 [FR] France ................. 76 06303
Dec. 10, 1976 [FR] France ................. 76 37240

[51] Int. Cl.$^2$ ............... C07C 53/34; C07C 145/00; C07C 31/34; C07C 21/18
[52] U.S. Cl. ............... 260/405.5; 260/408; 260/455 B; 260/465.7; 260/513.7; 260/526 N; 260/539 R; 260/543 R; 260/583 GG; 260/653; 260/653.3; 568/842; 560/227
[58] Field of Search ............ 260/408, 583 GG, 539 R, 260/513.7, 405.5, 465.7, 633, 487, 653.3, 653, 526 N; 252/431 C

[56] References Cited

U.S. PATENT DOCUMENTS

| B 351,455 | 2/1976 | Hayashi et al. ............ 260/633 X |
| 3,232,970 | 2/1966 | Hauptschein et al. ............ 260/408 |
| 3,681,413 | 8/1972 | Sweeney et al. ............ 260/408 X |
| 3,790,607 | 2/1974 | Lichstein ............ 260/408 |
| 3,979,469 | 9/1976 | Jager ............ 260/633 X |

FOREIGN PATENT DOCUMENTS

| 1,916,669 | 3/1970 | Fed. Rep. of Germany ....... 260/408 |
| 2,318,677 | 11/1974 | Fed. Rep. of Germany ....... 260/633 |
| 2,409,110 | 9/1974 | Fed. Rep. of Germany ....... 260/465.7 |
| 40-19,085 | 8/1965 | Japan ............ 260/633 X |
| 904,263 | 8/1962 | United Kingdom ............ 260/633 |

OTHER PUBLICATIONS

Moreau et al., "Chem Ab", Ab. No. 84:180,322 X (1976).

*Primary Examiner*—Daniel E. Wyman
*Assistant Examiner*—John J. Doll
*Attorney, Agent, or Firm*—Pennie & Edmonds

[57] ABSTRACT

The present invention relates to the process of preparing perfluoro functional compounds from a perfluorohalogenoalkane having the general formula:

$$R_F X$$

wherein $R_F$ is a saturated, unsaturated, straight, or branched chain perfluoroalkyl radical containing 2 to 12 carbon atoms, and X is selected from chlorine, bromine, or iodine, comprising reacting said perfluorohalogenoalkane with a functionalizing reagent in the presence of a metallic couple dispersed in a sulfoxide-type solvent, said metallic couple having the general formula:

$$M_1/M_2$$

wherein $M_1$ is metal selected from Group IB, IIA, IIB, or IIIA of the Periodic Table and $M_2$ is a metal having an electrochemical potential such that it can be deposited on metal $M_1$.

7 Claims, No Drawings

PROCESS FOR FUNCTIONALIZING PERFLUOROHALOGENOALKANES

BACKGROUND OF THE INVENTION

There is at the present time no convenient and economical method of preparing products such as perfluorocarboxylic acids, perfluorosulfonic acid and other perfluoro functional compounds. These acids, for example, are used as wetting agents or surfactants and also as intermediate materials for making treating agents for textiles, leathers, or papers, or for making products having surfactive properties. The perfluorosulfonic acids can also be used as acid catalysts in various reactions, such as alkylations.

To date, these products have been principally prepared by electrofluoroination, as described in J. Chem. Soc. (1956), page 173, in U.S. Pat. No. 3,732,398, and in Ind. Eng. Chem. (1951) 43, 2332. However, this technique is hard to put into practice and in the case of heavy acids results in very slight yields.

A chemical process to obtain these compounds is described in J. Fluorine Chem. 1975 5 (3) 265, and involves the reaction of $CO_2$ or $SO_2$ with perfluoro magnesium compounds. This technique, which uses organo magnesium compounds, is rather delicate and difficulty to carry out on a commercial basis.

SUMMARY OF THE INVENTION

The present invention provides a chemical process for preparing perfluorocarboxylic and perfluoroalkanesulfonic acids and other perfluoro functional compounds in a convenient and rapid manner with high yields. Briefly stated, the present invention comprises the process of preparing perfluoro functional compounds from a perfluorohalogenoalkane having the general formula:

$$R_F X$$

wherein $R_F$ is a saturated, unsaturated, straight, or branched chain perfluoroalkyl radical containing 2 to 12 carbon atoms, and X is selected from chlorine, bromine, or iodine, comprising reacting said perfluorohalogenoalkane with a functionalizing reagent in the presence of a metallic couple dispersed in a sulfoxide-type solvent, said metallic couple having the general formula:

$$M_1/M_2$$

wherein $M_1$ is a metal selected from Group IB, IIA, IIB, or IIIA of the Periodic Table and $M_2$ is a metal having an electrochemical potential such that it can be deposited on metal $M_1$.

DETAILED DESCRIPTION

Perfluorohalogenoalkanes constitute the starting products for the synthesis of functional perfluoro derivatives. While perfluoroiodoalkanes, $R_F I$, perfluorobromoalkanes, $R_F Br$, and perfluorochloroalkanes, $R_F Cl$, can be used, the perfluoroalkyl iodides are preferred because they are readily available. The perfluorohalogenoalkanes used have the general formula $R_F X$ where $R_F$ is a saturated, unsaturated, straight, or branched perfluoroalkyl radical having from 2 to 12 carbon atoms, and X is a chlorine, bromine or iodine atom.

The functionalizing agent reacted wit the perfluorohalogenoalkane will depend upon the particular perfluoro functional compound desired. Thus, for carboxylic acid derivatives, $CO_2$ is used and for the sulfinic acid derivatives, $SO_2$ is used. By standard chlorination techniques the sulfinic acid deriatives can be converted to the corresponding sulfonyl chlorides, $R_F SO_2 Cl$; which sulfonyl chlorides can be converted to the persulfonic acids, $R_F SO_3 H$, by conventional methods now used to convert sulfonyl chlorides to sulfonic acids. In like manner, to produce alcohol derivatives, aldehydes are used as the reactants and to produce acrylic derivatives, olefins are used. The particular functionalizing reagent to be used in each case will be dependent upon the end product desired and will be obvious to those skilled in this art.

It is essential that the reaction be carried out in the presence of a metallic couple $M_1/M_2$, dispersed in a sulfoxide solvent.

The metallic couple is made up of a metal, $M_1$, selected from Group IIA, IB, IIB, or IIIA of the Periodic classification of elements, and a metal, $M_2$, having such an electrochemical potential that it can be deposited on metal $M_1$; i.e., lower in the electromotive series of metals. Zinc is preferred as the metal $M_1$ and copper as metal $M_2$. The solvent can be any of the sulfoxide type with dimethylsulfoxide perferred.

The reaction can be carried out at ambient temperature preferably by the slow addition of perfluoroiodoalkanes, $R_F I$, to a dispersion of a metallic couple in dimethylsulfoxide (DMSO) and simultaneously introduction into this reaction medium of $CO_2$, $SO_2$ or other reagent. The functional product is isolated by suitable means. For example, decanting after acid hydrolysis for perfluorocarboxylic acids, chlorination in methanol medium for perfluoroalkanesulfonyl chlorides and the like procedures which are further described in the examples that follow.

The invention will be further described in connection with the following examples which are set forth for purposes of illustration only. While in these examples the metal $M_1$, in all instances, is zinc which is preferred, it will be understood that the other metals of Group IB, IIA, IIB, or IIIA are suitable and operative.

EXAMPLE 1

Preparation of perfluorohexyl sulfonyl chloride $C_6F_{13}SO_2Cl$

A. Preparation of Zn/Cu couple 2.4 of copper acetate $Cu(C_2H_3O_2).H_2O$ are dissolved in a mixture of 200 ml. of dimethylsulfoxide (DMSO) and 40 ml. of acetic acid kept at 45°–50° C. After dissolution, 78 g. of zinc powder are introduced with stirring and under a nitrogen atmosphere. The mixture is stirred for 30 minutes then the Zn/Cu couple is filtered and is washed four times with 60 ml. of DMSO.

B. Reaction of perfluorohexyl iodide with $SO_2$ in the presence of the Zn/Cu couple The Zn/Cu couple, prepared according to the method described above, is introduced into a 1-liter reactor, equipped with a stirrer, thermometer, gas intake tube, pouring funnel and reflux condenser and containing 400 ml. of DMSO. There is then introduced, in 4 hours, with stirring, while keeping the temperature at 45° C., 0.8 mole of $C_6F_{13}I$ (356.8 g.), 0.2 mole/hour, and $SO_2$ is bubbled in the reaction medium at a rate of 7 liters/hour for 4 hours which corresponds to about 1.15 mole of $SO_2$. At the end of the introduction of the two reagents, stirring is continued for 30 minutes, then about 300 g. of DMSO are evaporated under vacuum. The residue is dissolved with 300 ml. of water and a current of gaseous chlorine of 20 liters/hour is introduced for 3 hours (2.5 moles), while keeping the temperature at 45° to 50° C. by external cooling. A lower organic phase is formed which is decanted and distilled. 280 g. are obtained of a colorless liquid distilling at 55° C. under 25 mm. Hg and containing 96% $C_6F_{13}SO_2Cl$ determined by chromatographic analysis in the gaseous phase. The perfluorohexyl sulfonyl chloride was identified by mass spectrometry and infrared spectrography (IR) and the purity of the product determined by chromatographic analysis was confirmed by chemical analysis (elementary analysis, acidity by back titration). The rate of conversion of the $C_6F_{13}I$ to $C_6F_{13}SO_2Cl$ is 80.2%.

EXAMPLE 2

Preparation of $C_2F_5SO_2Cl$

In a reactor containing 100 ml. of DMSO and 20 g. of the Zn/Cu couple, prepared by the same method as set forth in Example 1, there are introduced in 2 hours, at 30° C., 79 g of $C_2F_5I$ (0.32 mole) and 0.4 mole of $SO_2$.

At the end of the introduction of the reagents, the DMSO is evaporated under vacuum, the residue is dissolved with 160 ml. of water and treated at 35° C., for 1 hour 30 minutes with chlorine (15 liters/hour). By decanting, a liquid is obtained which by distillation furnishes 40 g. of $C_2F_5SO_2Cl$ (boiling 55° C.) of 96% purity. The rate of conversion of $C_2F_5I$ to $C_2F_5SO_2Cl$ is 55%.

EXAMPLE 3

Preparation of $C_8F_{17}SO_2Cl$

Into the same reactor as that used for Example 1 and containing 100 ml. of DMSO and 20 g. of the Zn/Cu couple obtained according to the same method as that set forth in Example 1, there are introduced, in 2 hours, 0.2 mole of $C_8F_{17}I$ (109.2 g.) and 0.27 mole of $SO_2$ while keeping the temperature at 45° C. The reaction mixture is then treated in the same manner as in Example 1, and at the end of the chlorination a solid is obtained which is extracted with 250 ml. of chloroform. After evaporation of the chloroform and distillation, there is obtained 89 g. of a solid product (melting point 35° C., boiling $_{25\,mm.}$ 90° C.) containing 87.3% $C_8F_{17}SO_2Cl$ and 11% $C_8F_{17}I$. The rate of conversion of the $C_8F_{17}I$ to $C_8F_{17}SO_2Cl$ is 75% and the yield is 82.3%

EXAMPLE 4

Preparation of $C_{10}F_{21}SO_2Cl$

Into the same installation as that used in Example 1 and containing 100 ml. of DMSO and 20 g. of the Zn/Cu couple prepared by the method of Example 1, there are introduced 0.2 mole of $C_{10}F_{21}I$ in 1 hour 30 minutes (129.2 g.) and 0.27 mole of $SO_2$ in 2 hours, while keeping the temperature at 58° C.

At the end of the introduction of the reagents, the reaction medium is still stirred at 58° C. for 4 hours, and then the DMSO is evaporated under vacuum. The solid residue is dissolved with 700 ml. of water and then treated with chlorine (20 l./hour) for two hours at 30° to 40° C. During this chlorination, a solid is formed which is filtered and washed twice with 500 ml. of water. By drying under vacuum, there is thus obtained 98 g. of a white crystallized solid (melting point 77° C.) containing about 95% $C_{10}F_{21}SO_2Cl$ (rate of conversion 75%).

EXAMPLE 5

Preparation of $C_4F_9COOH$

A current of $CO_2$ (30 ml./min.) is bubbled in a dispersion of 20 g. of the Zn/Cu couple (prepared as in Example 1) in 20 ml. of DMSO, and then there is introduced, in 1 hour 30 minutes, a solution of 30 g. of $C_4F_9I$ (0.086 mole) in 20 ml. of DMSO while keeping the temperature of the reaction medium around 40° to 50° C. The reaction mixture is then treated twice with 60 ml of $CCl_4$ to eliminate the DMSO and then dried under vacuum. The residue is dissolved with 50 ml. of 50% hydrochloric acid and the perfluorocarboxylic acid decants in a lower phase which is distilled. There is thus obtained 9.5 g. of perfluoropentanoic acid (boiling $_{40\,mm.}$ 70° C.) identified by NMR and characterized by its salt of S-benzylthiouronium (melting point 180° C.) The rate of conversion of the $C_4F_9I$ to $C_4F_9COOH$ is 42%.

EXAMPLE 6

Preparation of $C_6F_{13}COOH$

Into a reactor containing 40 g. of the Zn/Cu couple (prepared by the method of Example 1) dispersed in 600 ml. of DMSO, $CO_2$ is bubbled at an hourly delivery rate of 6.5 liters. There is then introduced 0.4 mole of $C_6F_{13}I$ in 3 hours 30 minutes, while keeping the temperature at 20° C. by external cooling and then the reaction mixture is continued to be stirred for 3 hours. The reaction mixture is then filtered, the filtrate freed of the DMSO by evaporation under vacuum, and the residue is treated with 500 ml. of 50% hydrochloric acid. By decanting, an organic phase is obtained which is distilled. There is thus obtained 91.7 g. of perfluoroheptanoic acid identified by NMR and IR and by chemical analysis (boiling point $_{50\,mm.}$ 105° C.) The rate of conversion of the $C_6F_{13}I$ to $C_6F_{13}COOH$ is 63%.

EXAMPLE 7

Preparation of $C_8F_{17}COOH$

The mode of operation is completely identical with that of Example 6, except that after the hydrochloric acid treatment a solid is obtained which is filtered, dried and recrystallized in $CCl_4$. A 47% perfluorononanoic acid is obtained (melting point 71° C.)

EXAMPLES 8, 9 AND 10

Preparation of $C_4F_9COOH$

These examples relate to the preparation of perfluoropentanoic acid by reaction of $C_4F_9I$ and $CO_2$ in the presence of the metallic couples cadmium-zinc, lead-zinc, and mercury-zinc. These couples are prepared as follows: to a solution of each of cadmium acetate, lead acetate or mercuric chloride (0.003 mole) in 30 ml. of DMSO, kept at 80° C. with stirring, are added 20 g. of zinc powder, then 1.5 ml. of acetic acid. At the end of 30 minutes each the couple is washed three times with 50 ml. of DMSO.

Preparation of the $C_4F_9COOH$ was achieved by following exactly the mode of operation described in Example 5, but for each test replacing the Zn/Cu couple therein, respectively, with the couples Zn/Cd, Zn/Pb and Zn/Hg. In the three cases the results were completely identical with that of Example 5, i.e., the $C_4F_9COOH$ yield was 40 to 45%.

EXAMPLE 11

Preparation of butyl, perfluorohexyl trithiocarbonate

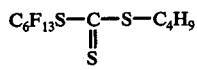

To a dispersion of 20 g. of the couple zinc/copper (prepared as in Example 1) in 30 ml. of DMSO is introduced, with stirring, and while maintaining the temperature below 20° C. by cooling with a bath at −15° C., a mixture of:
31 g. (0.07 mole) $C_6F_{13}I$
14.5 g. (0.077 mole)

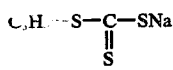

30 ml. DMSO

At the end of 5 minutes, all the iodoperfluorohexane has reacted and there is obtained, by decanting, a brown oil that is purified by chromatography on a silica column with petroleum ether as eluent. This product was identified by mass spectrometry, NMR, IR, and chemical analysis as being:

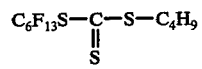

The yield is 60%.

Chlorination of this product in an aqueous medium and at ambient temperature leads to a dense, colorless derivative which decants. This lower phase was distilled (boiling $_{0.5\ mm}$ 82° C. and yielded a solid product (melting point 49° C.) which was identified as being

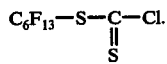

This chlorination made it possible to confirm the structure of the reaction product of the $C_6F_{13}I$ and of the sodium butyl trithiocarbonate.

EXAMPLE 12

Preparation of β-Perfluorohexyl Difluoroacrylic Acid 4.6 g. of brominated olefin, $C_6F_{13}CF\!=\!CF\ Br$, are added in an hour to a suspension of 3 g. of zinc-copper couple, prepared as in Example 1, in 10 ml. of DMSO and simultaneously a $CO_2$ current of 20 ml/minute is bubbled into the mixture while keeping the temperature of the reaction mixture between 30° and 40° C. The reaction mixture is then filtered, dissolved with 40 ml. of a 50% solution of hydrochloric acid and decanted. There is obtained 3.7 g. of a yellow oily product which was identified as being carboxylic acid $C_6F_{13}CF\!=\!CF\ COOH$ by comparison of IR and NMR spectra with those of an authentic sample of this acid obtained by another method.

EXAMPLE 13

Preparation of 2Perfluorohexyl Propionitrile, $C_6F_{13}C_2H_4CN$

A mixture of 43 g. of $C_6F_{13}I$, 7.5 g. of acrylonitrile, and 30 ml. of DMSO is introduced in 2 hours, at ambient temperature, in a vigorously stirred suspension of zinc-copper couple (prepared as in Example 1) in 150 ml. of DMSO. At the end of the introduction, the mixture is still stirred for 2 hours. There is obtained, after centrifuging and decanting, a colorless liquid, identified as being $C_6F_{13}C_2H_4CN$ by comparison of infrared, NMR, and mass spectra with those of a nitrile sample obtained by reaction of $C_6F_{13}C_2H_4I$ with sodium cyanide. The yield of the preparation is 50%.

EXAMPLE 14

Preparation of Ethyl Perfluoroheptanoate, $C_6F_{13}COOC_2H_5$ 44.6 g. of $C_6F_{13}I$ and 12 g. of ethyl carbonate are dissolved in 30 ml. of DMSO and added slowly to a dispersion of 18 g. of zinc-copper couple in 40 ml. of DMSO. At the end of the addition, which lasts 3 hours, the reaction mixture is centrifuged and by decanting a yellow liquid is obtained and identified by comparison of NMR and infrared spectra with that of a sample of $C_6F_{13}COOC_2H_5$ prepared by esterification of the acid, $C_6F_{13}COOH$, obtained by reaction of $C_6F_{13}I$ and of $CO_2$.

The yield of this preparation of 50%.

EXAMPLE 15

Preparation of Perfluorohexyl Methanol, $C_6F_{13}CH_2OH$

There are introduced, in 2 hours, at 60° to 70° C. 178 g. of $C_6F_{13}I$ to a stirred mixture of:
Paraformaldehyde — 14 g.
Zinc-Copper Couple — 39 g.
DMSO — 75 ml.

The reaction mixture is then dissolved with 350 ml. of water, acidified with 25 ml. of 50% sulfuric acid and decanted. 112 g. of liquid are obtained containing untransformed $C_6F_{13}I$ (2%), $C_6F_{13}H$ (50%), $C_6F_{12}$ (12%), and 23% $C_6F_{13}CH_2OH$. This latter product was identified by mass spectrometry. The rate of conversion of $C_6F_{13}I$ to $C_6F_{13}CH_2OH$ is 18.5%.

EXAMPLE 16

Preparation of 1-Perfluorohexyl Ethyl Alcohol, $C_6F_{13}CH(CH_3)OH$

There is introduced, in 2 hours, at 40° C., 178 g. of $C_6F_{13}I$ to a stirred mixture containing:
Acetaldehyde — 35 g.
Zinc-Copper Couple — 39 g.
DMSO — 75 ml.

At the end of the addition, the mixture is dissolved with 100 ml. of 6N sulfuric acid, then 200 ml. of water. By decanting, 123 g. are obtained of organic liquid containing:
55% — $C_6F_{13}H$
38% — $C_6F_{13}CH(CH_3)OH$ This product was identified by mass spectrometry. The rate of conversion of the $C_6F_{13}I$ to $C_6F_{13}CH(CH_3)OH$ is 32%.

While the invention has been described in connection with the preferred embodiments, it is not intended to limit the invention to the particular forms set forth, but, on the contrary, it is intended to cover such alternatives, modifications, and equivalents as may be included within the spirit and scope of the invention as defined by the appended claims.

What is claimed is:

1. A process of preparing perfluoro functional compounds which comprises; reacting
   (a) a perfluorohalogenoalkane having the general formula:

$R_F X$ wherein $R_F$ is a saturated, unsaturated, straight, or branched chain perfluoroalkyl radical having 2 to 12 carbon atoms, and X is a member selected from the group consisting of chlorine, bromine and iodine; and
   (b) a functionalizing agent selected from the group consisting of carbon dioxide, sulfur dioxide, aldehyde and olefin;
   (c) said reaction being effected in the presence of a metallic couple having the general formula:

$M_1/M_2$ wherein $M_1$ is metal selcted from Group IB, IIA, IIB, or IIIA of the Periodic Table, and $M_2$ is a metal having an electrochemical potential lower in the electromotive series of metals than said metals $M_1$; and
   (d) said reaction being effected in a sulfoxide solvent.

2. The process of claim 1 wherein the perflouorohalogenoalkane is a perfluoroalkyl iodide having 2 to 12 carbon atoms, the functionalizing reagent is selected from $CO_2$ or $SO_2$, the solvent is dimethylsulfoxide, and the metal, $M_1$, is zinc.

3. The process of claim 2 wherein the metal, $M_2$, is selected from copper, cadmium, lead, or mercury.

4. The process of claim 3 wherein the metal, $M_2$, is copper.

5. The process of claim 1 wherein there is used from 0.8 to 4.5 moles of said metallic couple per mole of perfluorohalogenoalkane.

6. The process of claim 1 wherein the perfluorohalogenoalkane is a perfluoroalkyl iodide having 2 to 12 carbon atoms, the functionalizing reagent is $CO_2$, the solvent is dimethylsulfoxide, the metallic couple is zinc-copper in a ratio of 0.9 to 1.5 moles per mole of perfluoroalkyl iodide, and the reaction is carried out at ambient temperature.

7. The process of claim 1 wherein the perfluorohalogenoalkane is a perfluoroalkyl iodide having 2 to 12 carbon atoms, the functionalizing reagent is $SO_2$, the solvent is dimethylsulfoxide, the metallic couple is zinc-copper in a ratio of 0.9 to 1.5 moles per mole of perfluoroalkyl iodide, and the reaction is carried out at ambient temperature.

UNITED STATES PATENT AND TRADEMARK OFFICE
CERTIFICATE OF CORRECTION

PATENT NO. : 4,098,806
DATED : July 4, 1978
INVENTOR(S) : Auguste Commeyras, Hubert Blancou and Patrice Moreau It is certified that error appears in the above-identified patent and that said Letters Patent are hereby corrected as shown below:

Column 1, line 18, reads "3,732,398", should read --2,732,398--

Column 2, line 51, reads "2.4", should read --2.4 g.--

Column 5, line 20, reads $C\ H\ -S-C-SNa$
$$\quad\quad\quad\quad\quad\quad\quad\quad\quad\quad\quad |$$
$$\quad\quad\quad\quad\quad\quad\quad\quad\quad\quad\quad S$$

should read $C_4H_9-S-C-SNa$
$$\quad\quad\quad\quad\quad\quad\quad\quad\quad\quad\quad |$$
$$\quad\quad\quad\quad\quad\quad\quad\quad\quad\quad\quad S$$

Signed and Sealed this

Fifteenth Day of May 1979

[SEAL]

Attest:

RUTH C. MASON
Attesting Officer

DONALD W. BANNER
Commissioner of Patents and Trademarks